(12) United States Patent
Haraguchi et al.

(10) Patent No.: US 12,232,833 B2
(45) Date of Patent: Feb. 25, 2025

(54) SURGICAL ROBOT SYSTEM, EXTERNAL FORCE ESTIMATION DEVICE, AND COMPUTER READABLE STORAGE MEDIUM

(71) Applicant: RIVERFIELD INC., Tokyo (JP)

(72) Inventors: Daisuke Haraguchi, Tokyo (JP); Kotaro Tadano, Tokyo (JP); Koki Aizawa, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 419 days.

(21) Appl. No.: 17/721,900

(22) Filed: Apr. 15, 2022

(65) Prior Publication Data

US 2022/0233261 A1    Jul. 28, 2022

Related U.S. Application Data

(63) Continuation of application No. PCT/JP2020/035626, filed on Sep. 18, 2020.

(30) Foreign Application Priority Data

Oct. 17, 2019   (JP) .................................. 2019-190341

(51) Int. Cl.
*A61B 34/30* (2016.01)
*A61B 90/50* (2016.01)
*B25J 13/08* (2006.01)

(52) U.S. Cl.
CPC .............. *A61B 34/30* (2016.02); *A61B 90/50* (2016.02); *B25J 13/085* (2013.01); *A61B 2034/305* (2016.02)

(58) Field of Classification Search
None
See application file for complete search history.

(56) References Cited

U.S. PATENT DOCUMENTS

| 2007/0151390 A1 | 7/2007 | Blumenkranz et al. |
| 2010/0094312 A1 | 4/2010 | Ruiz Morales et al. |

(Continued)

FOREIGN PATENT DOCUMENTS

| EP | 1915963 A1 * | 4/2008 | ............. A61B 34/30 |
| EP | 3205459 A1 | 8/2017 | |

(Continued)

OTHER PUBLICATIONS

Extended European Search Report dated Dec. 8, 2022 in Application No. 20877761.5.
Bauzano et al., "Active Wrists Endoscope Navigation in Robotized Laparoscopic Surgery", IEEE International Conference on Mechatronics, Apr. 14, 2009, pp. 1-6 (6 total pages).

(Continued)

*Primary Examiner* — Jaime Figueroa
*Assistant Examiner* — Arslan Azhar
(74) *Attorney, Agent, or Firm* — Sughrue Mion, PLLC

(57) ABSTRACT

A surgical robot system includes a surgical instrument including a shaft to be inserted through a trocar placed in a subject, an arm device that holds the surgical instrument and moves the surgical instrument with respect to the subject, a detector arranged at the arm device and configured to detect values of forces and torques acting on the surgical instrument; and a controller that calculates a value of a first external force that the surgical instrument receives from the trocar and a value of a second external force that is received from an object other than the trocar and that is abuttable on the surgical instrument, based on the values of forces and torques, and controls the arm device to move the surgical instrument, based on the value of the first external force and the value of the second external force.

16 Claims, 7 Drawing Sheets

(56) References Cited

U.S. PATENT DOCUMENTS

| | | | |
|---|---|---|---|
| 2017/0290601 | A1 | 10/2017 | Hongo et al. |
| 2019/0022857 | A1* | 1/2019 | Conus .................... B25J 9/0006 |
| 2019/0060019 | A1 | 2/2019 | Maret |
| 2019/0365489 | A1* | 12/2019 | Kasai ..................... A61B 1/055 |
| 2020/0289227 | A1 | 9/2020 | Jiang et al. |

FOREIGN PATENT DOCUMENTS

| | | |
|---|---|---|
| JP | 2009-522016 A | 6/2009 |
| JP | 2010-507792 A | 3/2010 |
| WO | 2015/079775 A1 | 6/2015 |
| WO | 2016/056339 A1 | 4/2016 |
| WO | 2018/159336 A1 | 9/2018 |
| WO | 2019/056871 A1 | 3/2019 |

OTHER PUBLICATIONS

Kim et al., "A 3-DOF Sensor to Estimate the Force Applied to the Tip of a Surgical Instrument", 18th International Conference on Advanced Robotics (ICAR), Jul. 2017, pp. 143-148 (6 total pages).

Kim et al., "A method to estimate the axial force applied to a surgical instrument tip considering the effect of the gravity", 11th Asian Control Conference (ASCC), Dec. 17, 2017, pp. 1246-1251 (6 total pages).

Jesus Mago et al., "Safe teleoperation of a laparoscope holder with dynamic precision but low stiffness", 2019 International Conference on Robotics and Automation (ICRA), IEEE, May 24, 2019, pp. 2693-2699.

Notice of Reasons for Refusal in the counterpart Japanese Application No. 2019-190341, dated Aug. 25, 2020.

International Search Report for PCT/JP2020/035626, dated Nov. 24, 2020.

\* cited by examiner

SURGICAL ROBOT SYSTEM, EXTERNAL FORCE ESTIMATION DEVICE, AND COMPUTER READABLE STORAGE MEDIUM

CROSS-REFERENCE TO RELATED APPLICATIONS

This Application is a Continuation Application of International Application No. PCT/JP2020/035626 filed on Sep. 18, 2020, which is based on Japanese patent application No. 2019-190341 filed on Oct. 17, 2019 with the Japanese Patent Office, the entire contents of each of which are incorporated by reference herein in their entireties.

BACKGROUND

The present disclosure relates to a surgical robot system, an external force estimation device, and a computer readable storage medium.

In recent years, endoscopic surgery using a surgical robot system is becoming widespread. Various surgical instruments, e.g., a laparoscope, an endoscope, a forceps, and so on, each of which are attached to an arm of the surgical robot system are used in endoscopic surgery.

SUMMARY

It is an aspect to provide a surgical robot system in which a size of a distal end of the surgical instrument is reduced and in which accuracy in measurement of an external force acting on the surgical instrument is improved, and that enhances comfort and safety for the subject.

According to an aspect of one or more embodiments, there is provided a surgical robot system comprising a surgical instrument including a shaft that is configured to be inserted through a trocar placed in a subject; an arm device configured to hold the surgical instrument and to move the surgical instrument with respect to the subject; a detector arranged at the arm device and configured to detect values of forces and torques acting on the surgical instrument; and a controller configured to calculate a value of a first external force that the surgical instrument receives from the trocar and a value of a second external force that is received from an object other than the trocar and that is abuttable on the surgical instrument, based on the values of the forces and torques, and based on a value of a resistance force acting between the trocar and the shaft, and configured to control the arm device to move the surgical instrument, based on the value of the first external force and the value of the second external force.

According to another aspect of one or more embodiments, there is provided an external force estimation device comprising at least one central processing unit configured to at least receive values of forces and torques detected by a detector provided at an arm device, the arm device being detachably connected to a surgical instrument having a shaft that is inserted through a trocar placed in a subject; calculate a value of a first external force that the surgical instrument receives from the trocar and a value of a second external force that is received from an object other than the trocar and that is abuttable on the surgical instrument, based on the values of the forces and torques, and based on a value of a resistance force acting between the trocar and the shaft; and transmit, to the arm device, control signals to control the arm device to move the surgical instrument, based on the value of the first external force and the value of the second external force.

According to another aspect of one or more embodiments, there is provided a non-transitory computer readable storage medium that stores program code which, when executed by one or more processors, causes the one or more processors to at least receive values of forces and torques detected by a detector provided at an arm device, the arm device being detachably connected to a surgical instrument having a shaft that is inserted through a trocar placed in a subject; calculate a value of a first external force that the surgical instrument receives from the trocar and a value of a second external force that is received from an object other than the trocar and that is abuttable on the surgical instrument, based on the values of the forces and torques, and based on a value of a resistance force acting between the trocar and the shaft; and transmit, to the arm device, control signals to control the arm device to move the surgical instrument, based on the value of the first external force and the value of the second external force.

BRIEF DESCRIPTION OF THE DRAWINGS

The above and/or other aspects will become apparent from the following description of various embodiments and with reference to the following drawings, in which.

DETAILED DESCRIPTION

Figure 1:
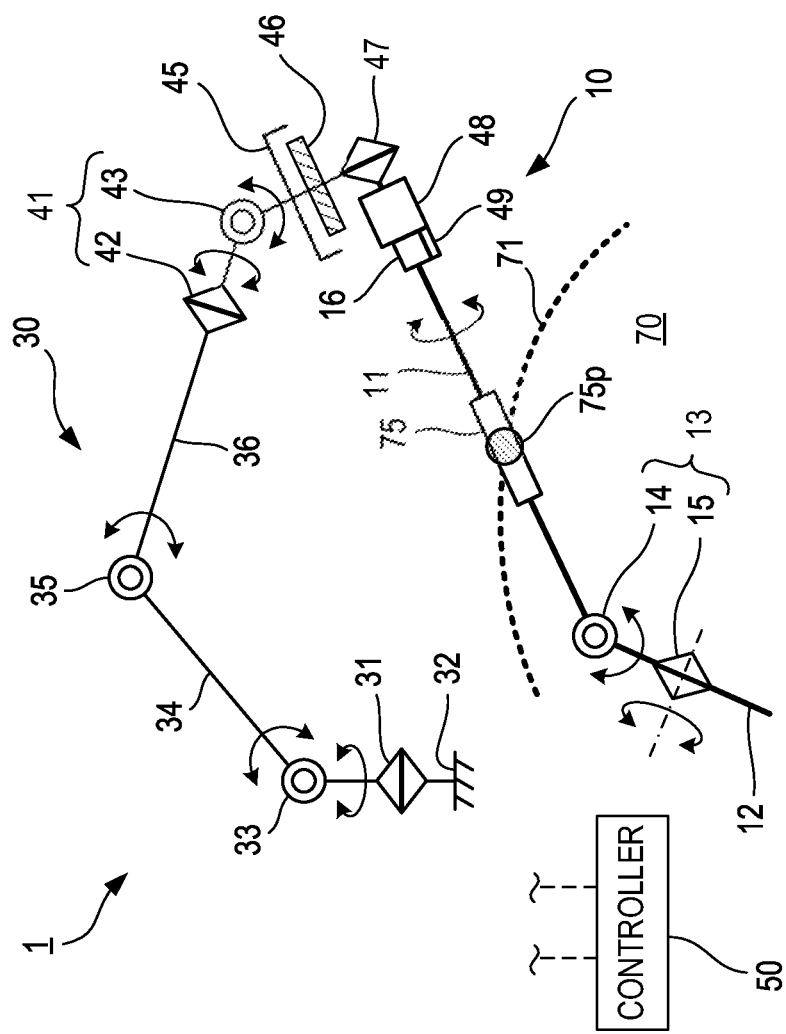
FIG. 1 is a schematic diagram explaining an example of a configuration of a surgical robot system according to various embodiments.

A trocar (or a port) through which a surgical instrument is inserted is placed in a subject (e.g., through an abdominal wall of the subject) to be subjected to endoscopic surgery. It is advantageous to reduce a load, specifically a force, applied to the subject by the surgical instrument during the endoscopic surgery.

Examples of the force applied may include a force applied to the abdominal wall of the subject via the trocar, and a force applied directly to the subject by a part of the surgical instrument not at a position corresponding to the trocar (e.g., a distal end of the surgical instrument or a shaft of the surgical instrument), i.e., by a part of the surgical robot system that is inserted into the subject.

In a related art method for detecting a force applied by the distal end of the surgical instrument, in other words a force applied to the distal end of the surgical instrument, a sensor arranged in the neighborhood of the distal end may measure the force applied and/or an external force applied to a joint of the distal end based on a driving force may be estimated.

However, the related art method of measuring the force by a sensor arranged in the neighborhood of the distal end of the surgical instrument makes it necessary to attach the sensor for measurement directly to the neighborhood of the distal end of the surgical instrument. Such an arrangement position of the sensor causes a problem in that the size of the distal end of the surgical instrument is increased and a problem in that the difficulty in sterilizing and washing the surgical instrument is increased. This increase in size and difficulty in sterilization results in further problems, such as increased costs for manufacture and use of the surgical instrument and thus the surgical robot system, as well as additional discomfort to and decrease in safety for the subject undergoing the surgery.

The related art method of estimating an external force applied to the joint has problems such as variability of accuracy in estimating the external force under the influence of, for example, friction within a mechanism of the surgical instrument and so on, and the inability to detect a force direction depending on arrangement of degrees of freedom of the surgical instrument.

Moreover, in the related art methods, a force applied to the shaft of the surgical instrument in a middle area of the surgical instrument cannot be measured or estimated, respectively. Thus, an estimated value of the external force could result in being smaller than an actual value of the external force.

It is an aspect to provide a surgical robot system in which a size of a distal end of the surgical instrument is reduced and in which accuracy in measurement of an external force acting on the surgical instrument is improved, and that enhances comfort and safety for the subject.

According to an aspect of various embodiments, a surgical robot system may comprise a surgical instrument used in surgery on a subject, the surgical instrument including a shaft formed in a long shape, the shaft being inserted through a trocar placed in the subject; an arm portion configured to grasp the surgical instrument in a movable manner with respect to the subject; a detector arranged at a position not where the shaft is present but where the arm is present and configured to detect values of forces and torques acting on the surgical instrument, the detector detecting the values of a length-direction force acting in a length direction of the shaft, a length-direction torque acting about the length direction, a first intersecting-direction force acting in a first intersecting direction that intersects with the length direction, a first intersecting-direction torque acting about the first intersecting direction, a second intersecting-direction force acting in a second intersecting direction that intersects with the length direction and with the first intersecting direction, and a second intersecting-direction torque acting about the second intersecting direction; and a calculator configured to calculate a value of a first external force that the surgical instrument receives from the trocar and a value of a second external force that is received from an object other than the trocar and that abuts the surgical instrument, based on the values of the length-direction force, the first intersecting-direction force, the second intersecting-direction force, the length-direction torque, the first intersecting-direction torque, and the second intersecting-direction torque, and on a value of a resistance force acting between the trocar and the shaft.

According to additional aspect of various embodiments, an external force estimation device and a non-transitory computer readable storage medium consistent with the surgical robot system are also provided.

The surgical robot system according to various embodiments make it possible to calculate the value of the first external force that the surgical instrument receives from the trocar and the value of the second external force that is received from an object other than the trocar and that abuts the surgical instrument, based on values of various external forces and torques detected by the detector and on the value of the resistance force acting between the trocar and the shaft.

Further, since the detector for detecting the values of the various external forces and torques is arranged at a position not where the shaft is present but where the arm is present, a size of the surgical instrument is facilitated, as compared with a related art device in which a sensor is arranged at a distal end of the surgical instrument.

A drive portion configured to drive a distal end of the shaft of the surgical instrument may be provided, the arm portion may comprise a holder configured to hold the surgical instrument, and the detector may be arranged between the drive portion and the holder.

Such an arrangement of the detector between the drive portion and the holder makes it less likely for the detector to detect a force and a torque caused by operation of the drive portion, as compared with a related art case in which, for example, the detector is arranged closer to the distal end than the drive portion is. Such an arrangement therefore improves the accuracy of detection by the detector.

A distal end external force detector configured to detect a value of a distal end external force, which is an external force that the distal end receives, may be provided, and the calculator may calculate a value of a shaft external force, which is an external force in the shaft received from an object other than the treatment tool and the trocar and that is abuttable on the surgical instrument, based on the value of the second external force and the value of the distal end external force.

Such provision of the distal end external force detector enables the calculator to calculate the value of the shaft external force, which is an external force in the shaft received from an object other than the treatment tool and the trocar and that is abuttable on the surgical instrument. Examples of the shaft external force may include a force applied by contact of a midsection of the shaft with an organ or the like of the subject, caused by relative movement of the surgical instrument with respect to the subject.

A storage may be provided which stores values of resistance forces each acting between the trocar of a different type and the shaft are stored in association with types of the trocar and a selector used to select the type of the trocar may be provided, and the calculator may acquire, from the storage, the value of the resistance force for the type of the trocar selected by the selector and may calculate the first external force and the second external force using the value of the resistance force acquired.

Such provision of the storage and the selector makes it easier to inhibit deterioration in accuracy of the calculated values of the first external force and the second external force, even when the trocar to be used is changed to a different trocar in which the resistance force acting between the trocar and the shaft is different.

The value of the first external force that the surgical instrument receives from the trocar and the value of the second external force that is received from an object other than the trocar and that abuts the surgical instrument may be calculated based on the values of the various external forces and torques detected by the detector and on the value of the resistance force acting between the trocar and the shaft. This calculation makes it possible to reduce the size of the distal end of the surgical instrument and to increase the accuracy in measurement of an external force acting on the surgical instrument, and thus enhance the safety of the surgical robot system.

Figure 2:
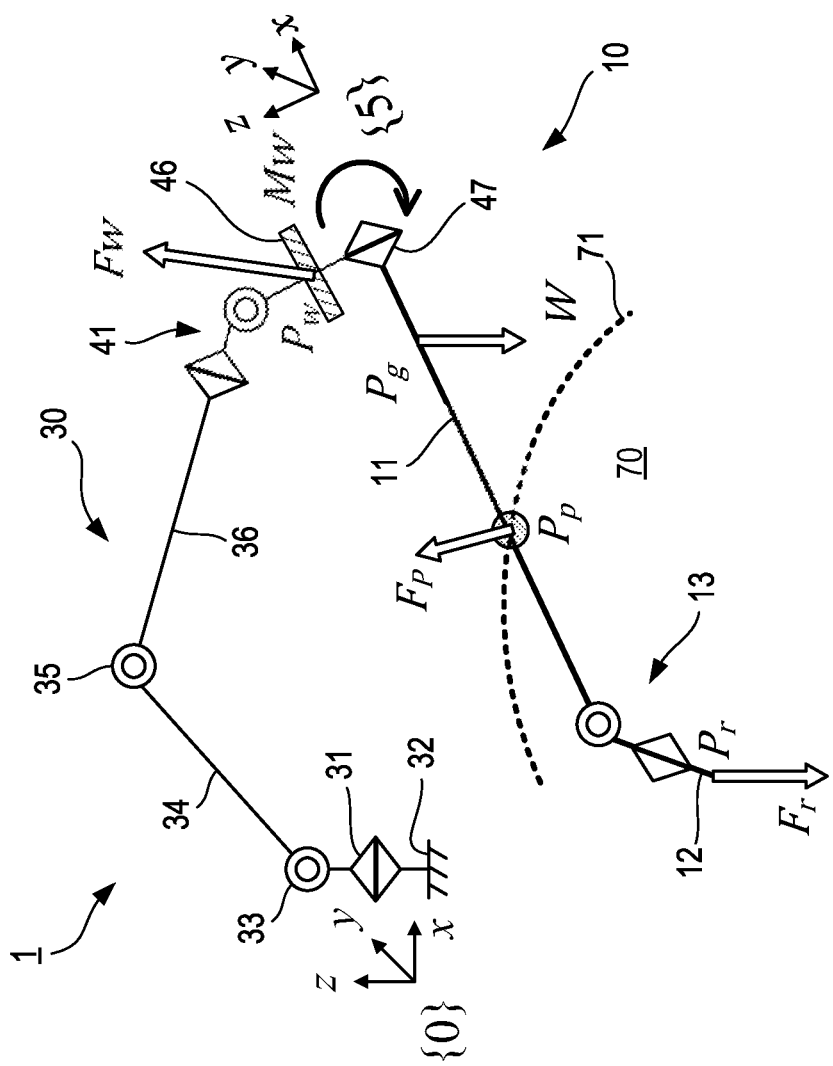
FIG. 2 is a diagram explaining a coordinate system, forces, and torques in the surgical robot system in FIG. 1.
Figure 3:
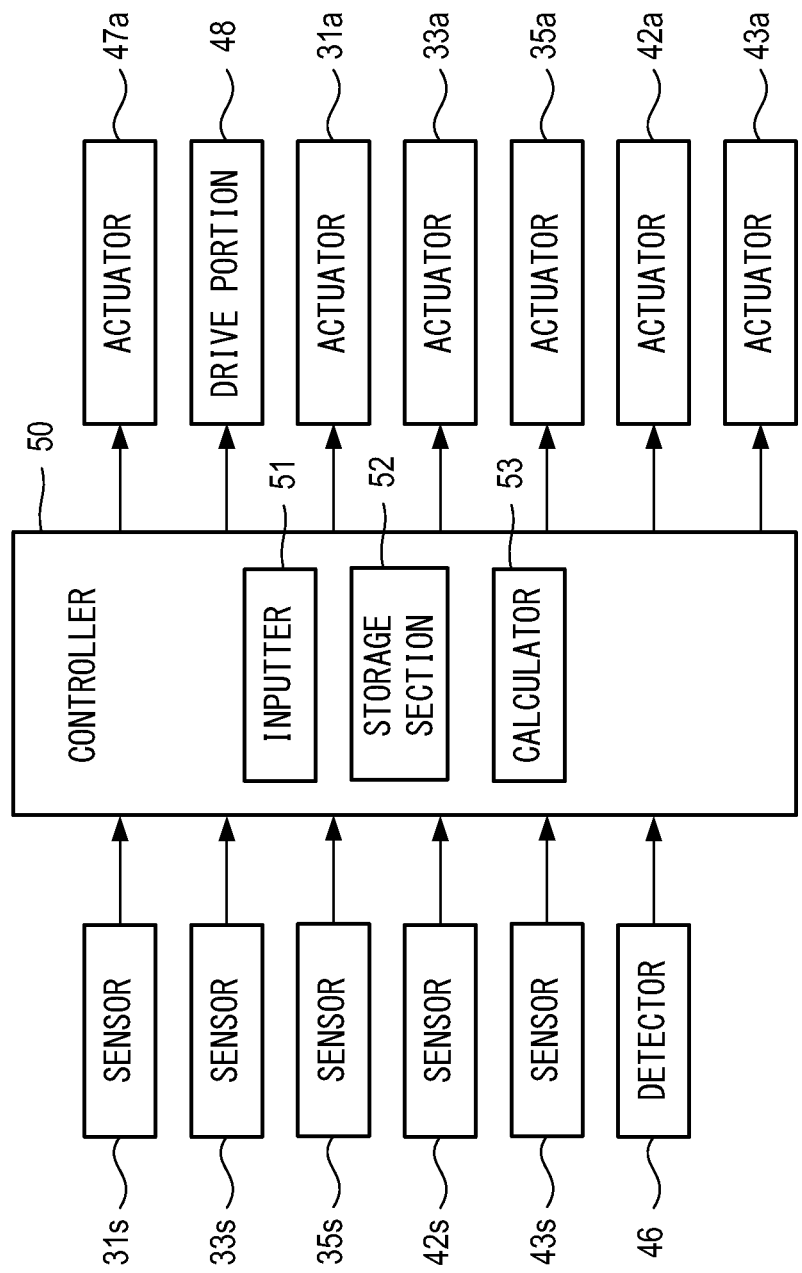
FIG. 3 is a block diagram explaining an example of a configuration of a controller of the surgical robot system in FIG. 1, according to various embodiments.

FIGS. 1-3 illustrate an example of a configuration of a surgical robot system according to various embodiments. A surgical robot system 1 is a surgery assisting robot or the like used in endoscopic surgery. As shown in FIG. 1, the surgical robot system 1 comprises a surgical instrument 10, an arm device 30, and a controller 50. The arm device 30 and the controller 50 each correspond to one example of an arm portion and an external force estimation device, respectively.

According to various embodiments, the surgical instrument 10 may be a treatment tool of any kind, such as, for example, a laparoscope, an endoscope or forceps, or other treatment tool used in endoscopic surgery. For ease of illustration, an explanation will be given of an example in which the surgical instrument 10 is a forceps. As shown in FIG. 1, the surgical instrument 10 comprises a shaft 11 and a main body 16.

The shaft 11 is a member extending in a tubular shape or a rod shape, and is inserted through a trocar 75 to thereby be inserted inside an abdominal wall 71 of a patient 70. The shaft 11 is provided with a forceps 12 at a distal end thereof, and a bend portion 13.

The trocar is hereinafter also referred to as a port. The patient 70 corresponds to one example of a subject.

The forceps 12 is a part at a distal end of the shaft 11, which is an end of the shaft 11 to be inserted into the patient 70. The forceps 12 is provided with an element for gripping an object.

The bend portion 13 has a shape of a cylinder or a column, with a first end thereof arranged on the forceps 12 and a second end thereof arranged on the shaft 11. The bend portion 13 has a configuration capable of bending laterally with respect to a direction in which the shaft 11 extends. FIG. 1 shows an example in which the bend portion 13 is configured with two rotating portions 14 and 15, rotation axes of which intersect with each other. In some embodiments, the rotation axes may intersect perpendicularly with each other. The configuration of the bend portion 13 is not particularly limited to this configuration.

The main body 16 is a part, in the surgical instrument 10, to be attached to and detached from the arm device 30. The main body 16 has a configuration through which a driving force to drive the forceps 12 and the bend portion 13 is transmitted from the arm device 30. A specific configuration of the main body 16 is not particularly limited.

The arm device 30 supports the surgical instrument 10 such that a position and an attitude thereof are changeable. The arm device 30 is controlled so that the surgical instrument 10 passes through a pivot position 75*p*, which is a specified relative position with respect to the arm device 30, even when the position and/or the attitude of the surgical instrument 10 are/is changed. The pivot position 75*p* is hereinafter also referred to as an immovable position. In some embodiments, the arm device 30 may move the surgical instrument 10 with six degrees of freedom.

As shown in FIG. 1, the arm device 30 comprises a rotating portion 31, a first arm rotating portion 33, a first arm 34, a second arm rotating portion 35, a second arm 36, a gimbal portion 41, a holder 45, a detector 46, a rotation support portion 47, a drive portion 48, and an attachment/detachment portion 49. In some embodiments, the arm device 30 is configured such that all of the rotating portion 31, the first arm rotating portion 33, the first arm 34, the second arm rotating portion 35, the second arm 36, the gimbal portion 41, the holder 45, the detector 46, the rotation support portion 47, the drive portion 48, and the attachment/detachment portion 49 are controlled so that the surgical instrument 10 passes through the pivot position 75*p*. However, it suffices if the surgical instrument 10 at least passes through the pivot position 75*p*, and thus, the arm device 30 does not necessarily have to be configured such that all of the rotating portion 31, the first arm rotating portion 33, the first arm 34, the second arm rotating portion 35, the second arm 36, the gimbal portion 41, the holder 45, the detector 46, the rotation support portion 47, the drive portion 48, and the attachment/detachment portion 49 are controlled actively.

The pivot position 75*p* may be predetermined or may be determined experimentally. In other words, the pivot position 75*p* may be a position provided in advance, or may be a position obtained based on a value measured by a sensor. In some embodiments, the pivot position 75*p* may be a position estimated based on behavior of the arm device 30.

The pivot position 75*p* generally coincides with a positon of an insertion hole in the abdominal wall 71 of the patient 70 who is subjected to endoscopic surgery. The trocar 75 through which the shaft 11 of the surgical instrument 10 is inserted is placed in the insertion hole.

In some embodiments, the trocar 75 comes into contact with the shaft 11 of the surgical instrument 10 inserted, and is not coupled and fixed to the arm device 30. That is, the trocar 75 is not held by the arm device 30.

In other words, the trocar 75 is used together with the arm device 30 that has no need for pivot positioning. That is, the arm device 30 has no need for alignment with an immovable point or position. Since the trocar 75 and the arm device 30 are not coupled and fixed to each other, the accuracy of a calculation of a first external force Fp and a second external force Fr may be improved as compared with a case in which the trocar 75 and arm device 30 are coupled and fixed to each other.

The rotating portion 31, the first arm rotating portion 33, the second arm rotating portion 35, the first joint 42 and the second joint 43 of the gimbal portion 41 are driven based on control signals from the controller 50. In some embodiments, the rotation support portion 47 and the drive portion 48 of the surgical instrument 10 may also be driven based on control signals from the controller 50.

The rotating portion 31 is a joint arranged in a portion where the arm device 30 is fixed to a base 32. The rotating portion 31 is provided with a sensor 31*s*, shown in FIG. 3, used to detect a phase of the rotating portion 31. The rotating portion 31 may have a configuration capable of being rotationally driven about a vertically extending rotation axis. However, the specific configuration is not particularly limited as long as the rotating portion 31 may be rotationally driven about the vertically extending rotation axis.

In some embodiments, the rotating portion 31 may be provided with an actuator 31*a* that generates a driving force using pressure of a gas, such as air, to cause the rotating portion 31 to move rotationally. The rotating portion 31 is rotationally driven by the driving force generated by the actuator 31*a*, based on a control signal from the controller 50.

The first arm rotating portion 33 is arranged between the rotating portion 31 and the first arm 34. The first arm rotating portion 33 has a configuration capable of being rotationally driven about a horizontally extending rotation axis. The first arm rotating portion 33 is provided with a sensor 33s, shown in FIG. 3, used to detect a phase of the first arm rotating portion 33.

In some embodiments, the first arm rotating portion 33 may be provided with an actuator 33a that generates a driving force using pressure of a gas, such as air. The first arm rotating portion 33 is rotationally driven by the driving force generated by the actuator 33a, based on a control signal from the controller 50.

Although the first arm rotating portion 33 is provided with the actuator 33a, in some embodiments, the actuator 33a may be omitted.

As shown in FIG. 1, the first arm 34 is arranged between the first arm rotating portion 33 and the second arm rotating portion 35. In some embodiments, the first arm 34 has a shape extending like a rod; however, the shape of the first arm 34 is not particularly limited to this shape.

The second arm rotating portion 35 is arranged between the first arm 34 and the second arm 36. The second arm rotating portion 35 has a configuration capable of being rotationally driven about a horizontally extending rotation axis. The second arm rotating portion 35 is provided with a sensor 35s, shown in FIG. 3, used to detect a phase of the second arm rotating portion 35.

In some embodiments, the second arm rotating portion 35 is provided with an actuator 35a that generates a driving force using pressure of a gas, such as air. The second arm rotating portion 35 is rotationally driven by the driving force generated by the actuator 35a, based on a control signal from the controller 50.

Although the second arm rotating portion 35 is provided with the actuator 35a, in some embodiments, the actuator 35a may be omitted.

As shown in FIG. 1, the second arm 36 is arranged between the second arm rotating portion 35 and the gimbal portion 41. In some embodiments, the second arm 36 has a shape extending like a rod; however, the shape of the second arm 36 is not particularly limited to this shape.

The gimbal portion 41 is arranged between the second arm 36 and the holder 45. The gimbal portion 41 comprises the first joint 42 and the second joint 43, rotation axes of which intersect with each other. In some embodiments, the rotation axes may intersect perpendicularly with each other.

The first joint 42 is arranged on a side, of the gimbal portion 41, closer to the second arm 36. The first joint 42 is arranged in an attitude such that a rotation axis thereof extends in a direction in which the second arm 36 extends. The first joint 42 is provided with a sensor 42s, shown in FIG. 3, used to detect a phase of the first joint 42.

The second joint 43 is arranged on a side, of the gimbal portion 41, closer to the holder 45. The second joint 43 is arranged in an attitude such that a rotation axis thereof extends in a direction intersecting with the direction in which the second arm 36 extends. In some embodiments, the rotation axis of the second joint 43 may extend in a direction intersecting perpendicularly with the direction in which the second arm 36 extends. The second joint 43 is provided with a sensor 43s, shown in FIG. 3, used to detect a phase of the second joint 43.

In some embodiments, the first joint 42 and the second joint 43 are respectively provided with an actuator 42a and an actuator 43a that generate a driving force using pressure of a gas, such as air, based on respective control signals from the controller 50, to cause the first joint 42 and the second joint 43, respectively, to move rotationally. However, in some embodiments, one or both of the actuator 42a and the actuator 43a may be omitted.

The holder 45 is arranged between the gimbal portion 41 and the rotation support portion 47. The holder 45 may have a configuration capable of holding the rotation support portion 47 and the drive portion 48. However, the specific configuration of the holder 45 is not particularly limited as long as the holder 45 is capable of holding the rotation support portion 47 and the drive portion 48.

The detector 46 is arranged between the holder 45 and the drive portion 48 held by the holder 45. The detector 46 is a force/torque sensor for detecting a force Fw acting on the surgical instrument 10 or on the holder 45 and a torque Mw acting on the surgical instrument 10 or on the holder 45, based on one or more control signals from the controller 50. The torque Mw is also referred to as a "moment". In some embodiments, a force torque sensor for detecting a force and a moment may be used as the detector 46, and a detection method and so on are not particularly limited.

The force Fw detected by the detector 46 comprises a component of a length-direction force acting in a length direction of the shaft 11, a component of a first intersecting-direction force acting in a first intersecting direction that intersects with the length direction, and a component of a second intersecting-direction force acting in a second intersecting direction that intersects with the length direction and with the first intersecting direction. The torque Mw comprises a component of a length-direction torque acting about the length direction, a component of a first intersecting-direction torque acting about the first intersecting direction, and a component of a second intersecting-direction torque acting about the second intersecting direction. In other words, the detector 46 is a force/torque sensor with six degrees of freedom.

As shown in FIG. 2, in a case where an orthogonal coordinate system {5} is set on the surgical instrument 10, the length direction, the first intersecting direction, and the second intersecting direction described above correspond respectively to an x-direction, a y-direction, and a z-direction in the coordinate system {5}.

Referring back to FIG. 1, a position where the detector 46 is arranged may be between the holder 45 and the drive portion 48 as described above, or may be a position further closer to the shaft 11 of the surgical instrument 10. When an arrangement position of the detector 46 is closer to the shaft 11, a calculation accuracy of the first external force Fp and the second external force Fr may be improved as compared with a case where the arrangement position is farther from the shaft 11.

The rotation support portion 47 rotatably supports the drive portion 48 about a central axis of the shaft 11 of the surgical instrument 10. In the state where the surgical instrument 10 is attached to the attachment/detachment portion 49, the rotation support portion 47 rotatably supports the drive portion 48 and the surgical instrument 10 about the central axis. The rotation support portion 47 is provided with an actuator 47a that generates a driving force to control rotation of the rotation support portion 47, based on a control signal from the controller 50.

The drive portion 48 is rotatably supported by the rotation support portion 47, and generates the driving force to drive at least one of the forceps 12 at the distal end of the shaft 11 or the bend portion 13 of the surgical instrument 10.

In some embodiments, a gas-pressure actuator for generating the driving force using pressure of a gas, such as air, may be arranged in the drive portion 48. In this case, the generated driving force is transmitted to the main body 16 of the surgical instrument 10 via the attachment/detachment portion 49, and is transmitted to at least one of the forceps 12 at the distal end of the shaft 11 or the bend portion 13 via a wire passed through the shaft 11.

A configuration of the drive portion 48 is not particularly limited to a specific configuration. Moreover, in some embodiments, a method of generating the driving force may be a method using pressure of a gas as described above or in other embodiments may be a method using an electric motor. However, these methods are only exemplary, and in other embodiments, other methods may be used.

The attachment/detachment portion 49 is arranged between the drive portion 48 and the surgical instrument 10. The attachment/detachment portion 49 has a configuration allowing for attachment/detachment of the main body 16 of the surgical instrument 10, and also has a configuration allowing for transmission of the driving force from the drive portion 48 to the main body 16. A specific configuration of the attachment/detachment portion 49 is not particularly limited.

The controller 50 calculates the first external force that the surgical instrument 10 receives from the trocar 75 and the second external force that is received from an object other than the trocar 75, the object being abuttable on the surgical instrument. For example, in some embodiments, the object other than the trocar that is abuttable on the surgical instrument may be a subject or may a portion other than the surgical instrument. For example, in some embodiments, the object other than the trocar that is abuttable on the surgical instrument may be a portion of the surgical robot system other than the surgical instrument. In addition, the controller 50 obtains positions and attitudes of the arm device 30 and the surgical instrument 10 by kinematic calculation, based on information detected by the sensor 31s, the sensor 33s, the sensor 35s, the sensor 42s, and the sensor 43s. The controller 50 outputs controls signals including respective drive commands to the actuator 31a, the actuator 33a, the actuator 35a, the actuator 42a, the actuator 43a and the actuator 47a based on the obtained positions and attitudes. External force information, such as a value of an external force calculated by a calculator 53 may be incorporated into the drive command to be outputted.

As shown in FIG. 1 and FIG. 3, the controller 50 may be implemented in hardware, firmware, or a combination of hardware and software. The controller 110 may be an information processor, such as a computer, which comprises at least one central processing unit (CPU), a read only memory (ROM), a random access memory (RAM), an input/output interface, and so on. Program code stored in a storage device, such as the ROM or the RAM, causes the CPU, the ROM, the RAM, and the input/output interface to work cooperatively to function as at least an inputter 51, a storage section 52, and the calculator 53. In some embodiments, the controller 50 may include one or more controllers capable of being programmed to perform a function. The controller may include a memory such as the RAM, the ROM, and/or another type of dynamic or static storage device (e.g., a flash memory, a magnetic memory, and/or an optical memory) that stores information and/or instructions for use by controller 50. The memory stores information and/or software related to the operation and use of the surgical robot system 1. In some embodiments, the memory may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive. The memory may store program code which when read and executed by the controller 50, causes the controller 50 to perform the various functions of the controller 50.

The inputter 51 (e.g., the information processor) receives input of information on the force Fw and the torque Mw that are detected and outputted by the detector 46. Specifically, values of the length-direction force, the first intersecting-direction force, and the second intersecting-direction force, and values of the length-direction torque, the first intersecting-direction torque, and the second intersecting-direction torque are received from the detector 46. The inputter 51 also receives detection signals from the sensor 31s, the sensor 33s, the sensor 35s, the sensor 42s, and the sensor 43s.

The storage section 52 (e.g., the information processor in combination with RAM) stores in advance a value of a resistance force 5Fpx acting between the trocar 75 and the shaft 11 of the surgical instrument 10, and a value of a gravity W acting on the surgical instrument 10. A value of weight or mass may be used as the value of the gravity W. The resistance force takes a different value depending on combination of the trocar 75 and the shaft 11. When the trocar 75 and the surgical instrument 10 to be used in the surgical robot system 1 are known, the resistance force is measured or calculated, and is stored in advance in the storage section 52 (e.g., the RAM or the ROM).

The calculator 53 (e.g., the information processor in combination with RAM) calculates a value of the first external force and a value of the second external force based on the information on the force Fw and the torque Mw inputted to the inputter 51 (i.e., received from the detector 46) and on the value of the resistance force stored in advance in the storage section 52 (e.g., the RAM or the ROM). Specific details of the calculation of the value of the first external force and the value of the second external force will be described below.

Next, an explanation will be given of calculation of the value of the first external force and the value of the second external force in the surgical robot system 1 having the above-described configuration. First, derivation of equations for calculating the value of the first external force and the value of the second external force will be described with reference to FIG. 2.

To begin with, an equation (1) of equilibrium of a translational force as seen from the coordinate system {5} shown in FIG. 2 and an equation (2) of equilibrium of moment about the detector 46 are obtained. The equation (1) and the equation (2) are provided below. Here, the coordinate system {5} is an orthogonal coordinate system set on the surgical instrument 10, and the direction in which the shaft 11 extends is set as the x-direction.

[Mathematical Expression 1]

$$F_r + F_p + W + F_w = 0 \tag{1}$$

$$M_w + (P_r - P_w) \times F_r + (P_p - P_w) \times F_p + (P_g - P_w) \times W = 0 \tag{2}$$

In the equations (1) and (2) above, Fr represents an external force when the second external force to be obtained acts concentratedly on the forceps 12 at the distal end of the shaft 11. In other words, the second external force to be obtained is assumed to act concentratedly on the forceps 12 at the distal end of the shaft 11 as a resultant force obtained by combining a shaft external force acting also on other portions. Pr represents a position vector of the forceps 12 at the distal end of the shaft 11. Fp represents an external force acting on a portion of the shaft 11 facing the insertion hole, and Pp represents a position vector of the insertion hole. W represents the gravity acting on the surgical instrument 10, and Pg represents a position vector of the center of gravity of the surgical instrument 10. Fw represents a force acting on the holder 45, and is a force detected by the detector 46. Mw represents a moment acting on the holder 45, and is a moment detected by the detector 46. The external force acting on the portion of the shaft 11 facing the insertion hole corresponds to one example of the first external force.

Here, unknowns are only Fp and Fr. Other values may be measured by the sensors or estimated by calculation based on robot forward kinematics. Eliminating Fr from the above equations (1) and (2) yields the following equation (3).

[Mathematical Expression 2]

$$(P_p - P_r) \times F_p = -(P_g - P_r) \times W - (P_w - P_r) \times F_w - M_w \quad (3)$$

As shown in FIG. 2, a coordinate system {0} is set on the arm device 30. The equation (3) is considered in the coordinate system {5}, and an attitude matrix of the coordinate system {0} as seen from the coordinate system {5} is created as described below in Mathematical Expression 3. Using this attitude matrix, the equation (3) may be expressed as the following equation (4).

[Mathematical Expression 3]

$$_0^5R$$

[Mathematical Expression 4]

$$\{_0^5R(P_p - P_r)\} \times (_0^5RF_p) = -\{_0^5R(P_g - P_r)\} \times (_0^5RW) - \{_0^5R(P_w - P_r)\} \times (_0^5RF_w) - _0^5RM_w \quad (4)$$

Given that the equation (4) is expressed using the following mathematical expression and that the right side of the equation (4) is M, the equation (4) may be expressed as an equation (5).

$$_0^5RF_p = {}^5F_p \quad \text{[Mathematical Expression 5]}$$

[Mathematical Expression 6]

$$_0^5R(P_p - P_r) \times {}^5F_p = M \quad (5)$$

When the equation (5) is expressed using the following mathematical expression, the equation (5) is expressed as an equation (6).

[Mathematical Expression 7]

$$_0^5R(P_p - P_r) = [l_{px}, l_{py}, l_{pz}]^T$$

[Mathematical Expression 8]

$$\begin{bmatrix} l_{px} \\ l_{py} \\ l_{pz} \end{bmatrix} \times \begin{bmatrix} {}^5F_{px} \\ {}^5F_{py} \\ {}^5F_{pz} \end{bmatrix} = \begin{bmatrix} l_{py}{}^5F_{pz} - l_{pz}{}^5F_{py} \\ l_{pz}{}^5F_{px} - l_{px}{}^5F_{pz} \\ l_{px}{}^5F_{py} - l_{py}{}^5F_{px} \end{bmatrix} = \begin{bmatrix} M_x \\ M_y \\ M_z \end{bmatrix} \quad (6)$$

The equation (6) is an equation of an equilibrium of a moment about Pr. The equation (6) is a system of simultaneous equations from a skew-symmetric matrix. Three variables 5Fpx, 5Fpy, and 5Fpz cannot be solved independently by the equation (6) alone.

Here, 5Fpx is a resistance force acting between the trocar 75 and the shaft 11 of the surgical instrument 10. Thus, a value of 5Fpx can be set in advance as an appropriate condition or value in consideration of a structure of the trocar 75, external force compensation performance of the arm device 30, and so on. Examples of the value of 5Fpx may include the following three conditions. In the following conditions, f represents a constant, and μ represents a coefficient of friction.

$$^5F_{px} = 0$$

$$^5F_{px} = f$$

$$^5F_{px} = \mu N \quad \text{[Mathematical Expression 9]}$$

where $N = \sqrt{{}^5F_{px}{}^2 + {}^5F_{pz}{}^2}$

For example, when the condition 5Fpx=0 is used, solving for 5Fpy and 5Fpz of the equation (6) yields the following equations (7) and (8).

[Mathematical Expression 10]

$$^5F_{py} = \frac{M_z}{l_{px}} \quad (7)$$

$$^5F_{pz} = -\frac{M_y}{l_{px}} \quad (8)$$

Further, solving for Fry and Frz using a relation between the above equations (7) and (8) and the equation (1) results as shown in the following equations (9) and (10).

[Mathematical Expression 11]

$$F_{ry} = -F_{py} - W_y - F_{wy} \quad (9)$$

$$F_{rz} = -F_{pz} - W_z - F_{wz} \quad (10)$$

An external force Frx parallel to the shaft 11 generated at the forceps 12 at the distal end of the shaft 11 may be obtained from the following relational equation (11) of a resultant force in terms of an x-direction component of the detector 46. The equation (11) shows an equation with the term of Fpx on the left, so as to facilitate understanding when a condition other than 5Fpx=0 is used.

[Mathematical Expression 12]

$$F_{wx} = -F_{rx} - F_{px} - W_x \quad (11)$$

When the condition 5Fpx=f is used or when the condition 5Fpx=μN is used, solving for 5Fpy and 5Fpz of the equation (6) yields equations for obtaining respective values. As for Fry, Frz, and Frx, equations for obtaining respective values are yielded in a manner similar to the above and a repeated description thereof is omitted for conciseness.

The methods of obtaining the values of 5Fpy, 5Fpz, Fry, Frz, and Frx may be those using an analytical approach based on deformation of the equations as described above, or may be those using simultaneous equations approach, such as a numerical analysis method using a computer.

Next, an explanation will be given of calculation of the value of the first external force and the value of the second external force in the surgical robot system 1. Here, Fp as described above corresponds to the first external force, and Fr as described above corresponds to one example of the second external force. The calculator 53 (i.e., the information processor in combination with the RAM) in the controller 50 performs an operation of calculating the above-described Fp and Fr.

The controller 50 acquires, from the storage section 52, the value of the gravity W acting on the surgical instrument 10 to be used in calculating Fp and Fr, and also performs a process of acquiring, from the detector 46, the force Fw acting on the holder 45 and the moment Mw acting on the holder 45.

Further, the controller 50 performs an operation of obtaining position vectors of Pr, Pp, Pg, and Pw to be used in calculating Fp and Fr. When performing the operation, the controller 50 performs an arithmetic process for acquiring detection signals to be used in calculating the position vectors and control signals for controlling an attitude of the bend portion 13. The detection signals are outputted from the sensor 31s, the sensor 33s, the sensor 35s, the sensor 42s, and the sensor 43s.

Additional information such as mathematical equations used in obtaining the position vectors and size information including the length and the shape of the first arm 34 and the other components of the arm device 30 are stored in advance in the storage section 52 and are used by the controller 50.

In the embodiment of FIGS. 1-3, in obtaining the position vectors of Pr, Pp, Pg, and Pw, the sensor 31s, the sensor 33s, the sensor 35s, the sensor 42s, and the sensor 43s for detecting the respective phases are used. However, the control signals for controlling the attitude of the arm device 30 may be used instead of outputs of the sensors for detecting the respective phases.

Similarly, although the control signals for controlling the attitude of the bend portion 13 are used in the embodiment of FIGS. 1-3, outputs of the sensors for detecting the attitude of the bend portion 13 may be used instead of the control signals.

As for the equations used in obtaining the position vectors and as for parameters included in the mathematical equations, various equations and parameters may be used according to the types and the shapes of the arm device 30 and the surgical instrument 10, and limitation to those described above with reference to the embodiment illustrated in FIGS. 1-3 is not intended.

Subsequently, the calculator 53 in the controller 50 performs an operation of calculating Fp and Fr using the position vectors of Pr, Pp, Pg, and Pw, the gravity W, the force Fw, the moment Mw, the above-described equations (7), (8), (9), (10), and (11), and so on.

The surgical robot system 1, the controller 50, and the program configured as described above, make it possible to calculate the value of the first external force Fp that the surgical instrument 10 receives from the trocar 75 and the value of the second external force Fr that is received from an object other than the trocar 75 and that is abuttable on the surgical instrument, based on values of various external forces and torques detected by the detector 46 and on the value of the resistance force 5Fpx acting between the trocar 75 and the shaft 11.

Since the detector 46 for detecting the values of various external forces and torques is arranged at a position not where the shaft 11 is present but where the arm device 30 is present (i.e., at a positon between the holder 45 and the drive portion 48), the size of the surgical instrument 10 may be reduced as compared with a case in which a sensor or detector is arranged on the surgical instrument 10, e.g., at the forceps or on the distal end of the surgical instrument 10.

As compared with a case where, for example, the detector 46 is arranged closer to the forceps 12 than the drive portion 48 is, arranging the detector 46 between the drive portion 48 and the holder 45 makes it less likely for the detector 46 to detect a force and a torque caused by operation of the drive portion 48. In other words, accuracy of detection by the detector 46 is improved.

Each component of the external force may be obtained independently based on various information from the detector 46, which is the force/torque sensor with six degrees of freedom. Thus, theoretically speaking, there occurs no case where the external force acting on the forceps 12 at the distal end of the shaft 11, and/or on the trocar 75 is undercalculated.

The surgical robot system 1 is controlled using the calculated value of the first external force Fp and the calculated value of the second external force Fr. For example, at least one actuator of the actuator 31a, the actuator 33a, the actuator 35a, the actuator 42a, the actuator 43a and the actuator 47 is controlled according to control signals from the controller 50, based on the calculated value of the first external force Fp and/or the calculated value of the second external force Fr. This control permits using the first external force Fp and/or the second external force Fr to provide force feedback and to improve safety by, for example, appropriately setting thresholds for the control of the surgical robot system 1 even when some uncertainty is contained in the gravity W acting on the surgical instrument 10, a frictional force Fpx of the trocar 75, and so on.

For example, it becomes possible to achieve an operation such as maintaining the position and the attitude of the forceps 12 at the distal end of the shaft 11 without yielding to the external force acting on the shaft 11 of the surgical instrument 10 while suppressing the first external force Fp that the surgical instrument 10 receives from the trocar 75 below a certain level.

It is possible to detect the first external force Fp that the surgical instrument 10 receives from the trocar 75 and the second external force Fr that is received from an object other than the trocar 75 and that is abuttable on the surgical instrument in a significantly distinguishable manner. Thus, enhancement of the safety in and out of the visual field during surgery is facilitated by presenting the first external force Fp and the second external force Fr to a manipulator of the surgical robot system 1. For example, the first external force Fp and/or the second external force Fr may be displayed on a display of the controller 50 or an audible alert may be provided such that a surgeon manipulating the surgical robot system 1 may be given feedback during a surgical operation using the surgical robot system 1.

Figure 4:
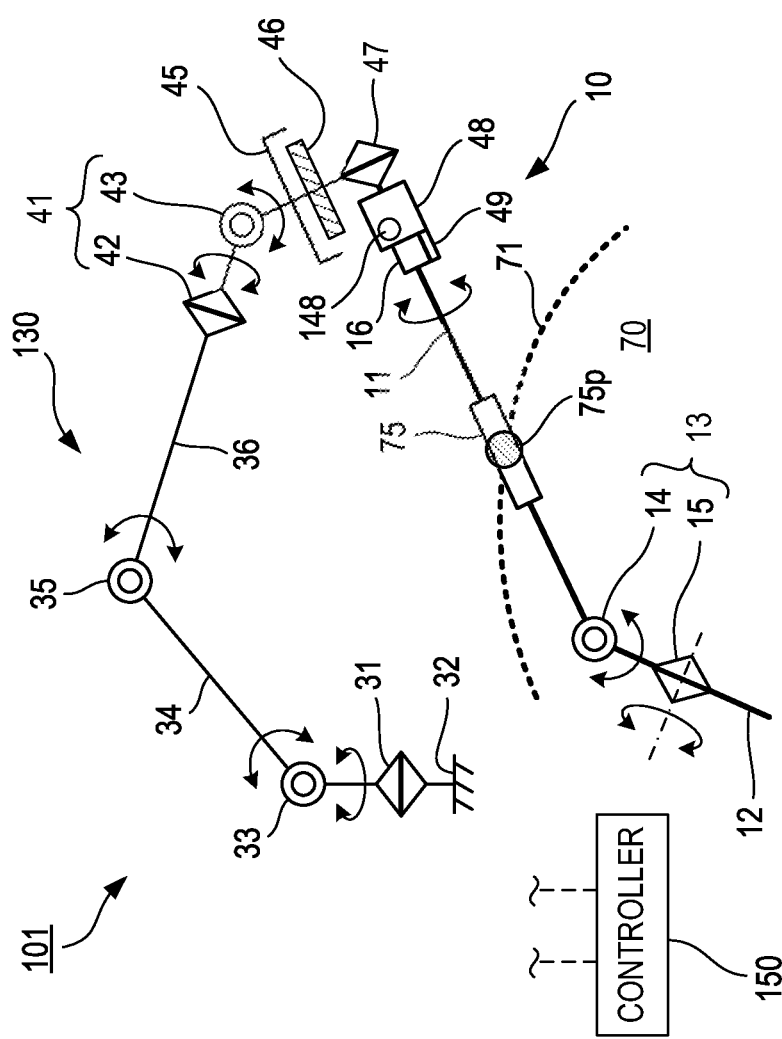
FIG. 4 is a schematic diagram explaining another example of a configuration of a surgical robot system according to various embodiments.
Figure 5:
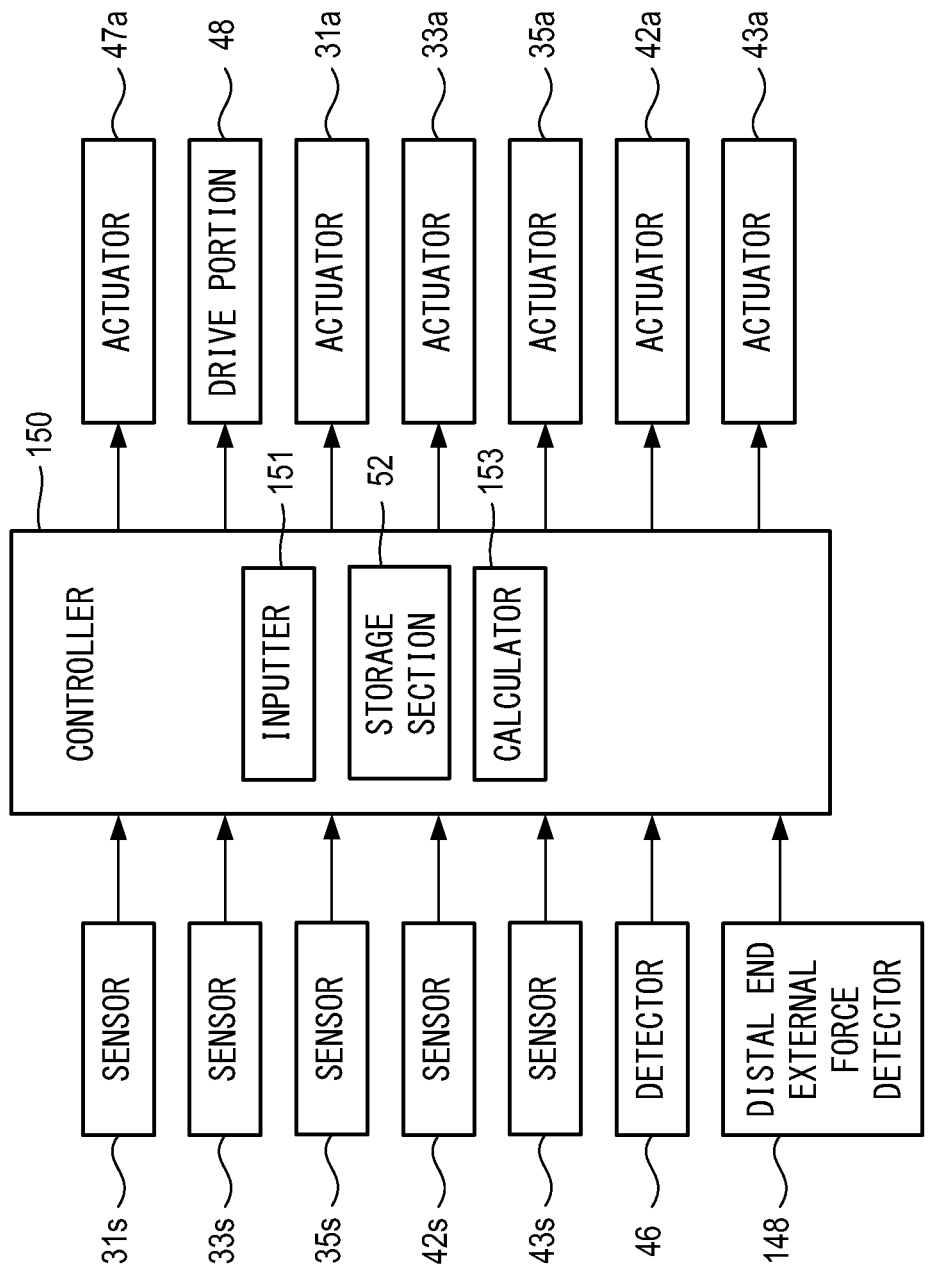
FIG. 5 is a block diagram explaining an example of a configuration of a controller of the surgical robot system in FIG. 4, according to various embodiments.

FIGS. 4-5 illustrate another example of a configuration of a surgical robot system according to various embodiments. A basic configuration of the surgical robot system illustrated in FIGS. 4-5 is similar to that of the embodiment illustrated with reference to FIGS. 1-3 and like reference numbers refer to like elements/components and repeated description thereof will be omitted for conciseness. However a method for obtaining the external force received by the forceps at the distal end of the shaft of the surgical instrument is different from that of the embodiment illustrated with respect to FIGS. 1-3. Thus, an explanation will be given of the method for obtaining the external force received by the forceps at the distal end of the shaft 11 of the surgical instrument with reference to FIG. 4 and FIG. 5.

As shown in FIG. 4, a surgical robot system 101 comprises the surgical instrument 10, an arm device 130, and a controller 150. The controller 150 corresponds to one example of an external force estimation device.

The arm device 130 comprises the rotating portion 31, the first arm rotating portion 33, the first arm 34, the second arm rotating portion 35, the second arm 36, the gimbal portion 41, the holder 45, the detector 46, the rotation support portion 47, the drive portion 48, the attachment/detachment portion 49, and a distal end external force detector 148. The distal end external force detector 148 is a sensor for detecting a value of a distal end external force Ft, which is an external force received by the forceps 12 at the distal end of the shaft 11 of the surgical instrument 10.

In a case where the drive portion 48 comprises a gas-pressure actuator for generating a driving force that drives the forceps 12 at the distal end of the shaft 11 and the bend portion 13 using pressure of a gas, such as air, the distal end external force detector 148 includes a sensor for detecting a displacement of a piston and so on in the gas-pressure actuator and a sensor for detecting the pressure of gas within a cylinder of the piston.

A position and a detection method of the distal end external force detector 148 is not particularly limited as long as the distal end external force detector 148 may detect the external force Ft acting on the forceps 12 at the distal end of the shaft 11. For example, in some embodiments, the distal end external force detector 148 may be a sensor that is arranged in a neighborhood of the forceps 12 at the distal end of the shaft 11 in the surgical instrument 10 to detect the external force Ft acting on the forceps 12 at the distal end of the shaft 11.

As shown in FIG. 4 and FIG. 5, the controller 150 is an information processor, such as a computer, which comprises a central processing unit (CPUO, a ROM, a RAM, an input/output interface, and so on.

Program code stored in a storage device, such as the ROM or the RAM, causes the CPU, the ROM, the RAM, and the input/output interface to work cooperatively to function as at least an inputter 151, the storage section 52, and a calculator 153.

As compared with the inputter 51, the inputter 151 further receives information on the distal end external force Ft from the distal end external force detector 148 that is applied to the forceps 12 at the distal end of the shaft 11 and detected by the distal end external force detector 148.

The calculator 153 calculates a value of the first external force Fp and a value of the second external force Fr based on the information on the force Fw and the torque Mw inputted to the inputter 151, based on the information on the distal end external force Ft, and on the value of the resistance force stored in advance in the storage section 52.

The calculator 153 performs an operation similar to that of the calculator 53 when calculating the value of the first external force Fp and the value of the second external force Fr. When calculating a value of the distal end external force Ft acting on the forceps 12, the calculator 153 performs an operation based on the information on the distal end external force Ft detected and outputted by the distal end external force detector 148. Furthermore, calculation of the shaft external force, which is an external force received from an object other than the forceps 12 and the trocar 75 and that is abuttable on the surgical instrument, is performed using the calculated second external force Fr and the calculated distal end external force Ft acting on the forceps 12. Given that a resultant force of the shaft external force is Fs, Fs may be obtained using the following equation.

$$F_s = F_r - F_t \quad \text{[Mathematical 13]}$$

The configuration illustrated in FIGS. 4-5 with the distal end external force detector 148 provided enables the calculator 153 to calculate a value of the shaft external force, which is an external force in the shaft 11 received from an object other than the forceps 12 and the trocar 75 and that is abuttable on the surgical instrument. Examples of the shaft external force may include a force applied due to contact of a midsection of the shaft 11 with an organ or the like of the patient 70, which is caused by relative movement of the surgical instrument 10 with respect to the patient 70.

In addition, use of the distal end external force Ft obtained by the distal end external force detector 148 as a reference signal facilitates further improvement in accuracy of the first external force Fp and the second external force Fr to be calculated, as compared with a case where the distal end external force detector 148 is omitted.

Figure 6:
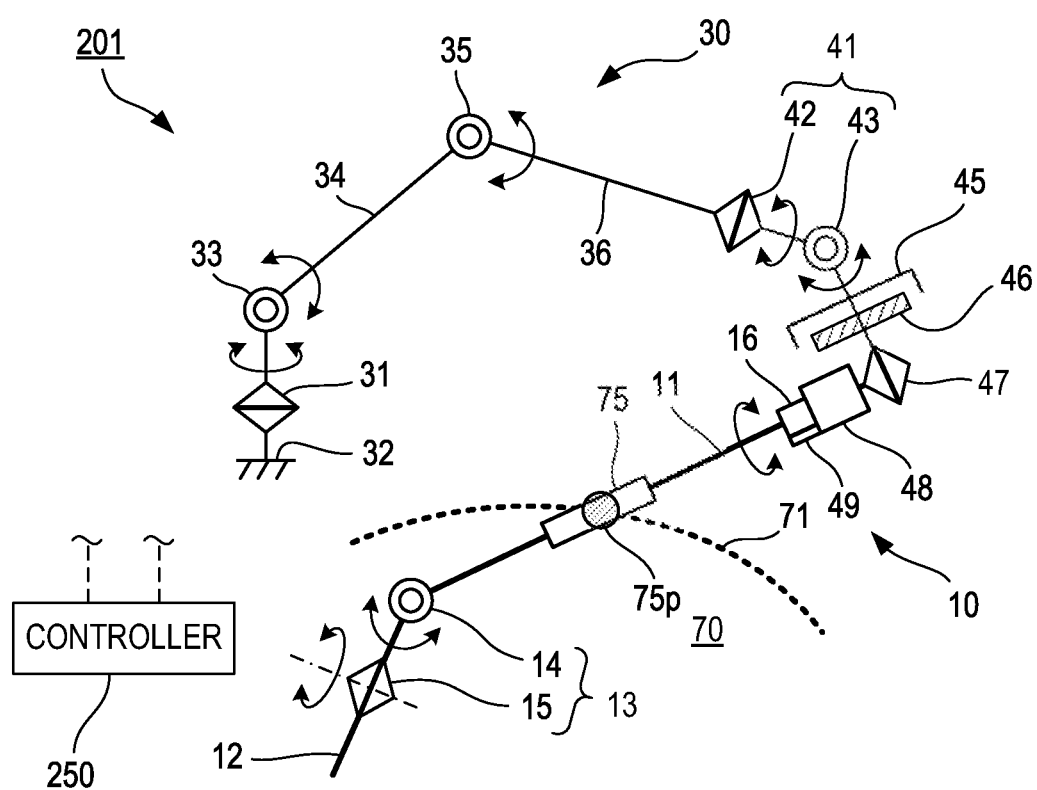
FIG. 6 is a schematic diagram explaining another example of a configuration of a surgical robot system according to various embodiments.
Figure 7:
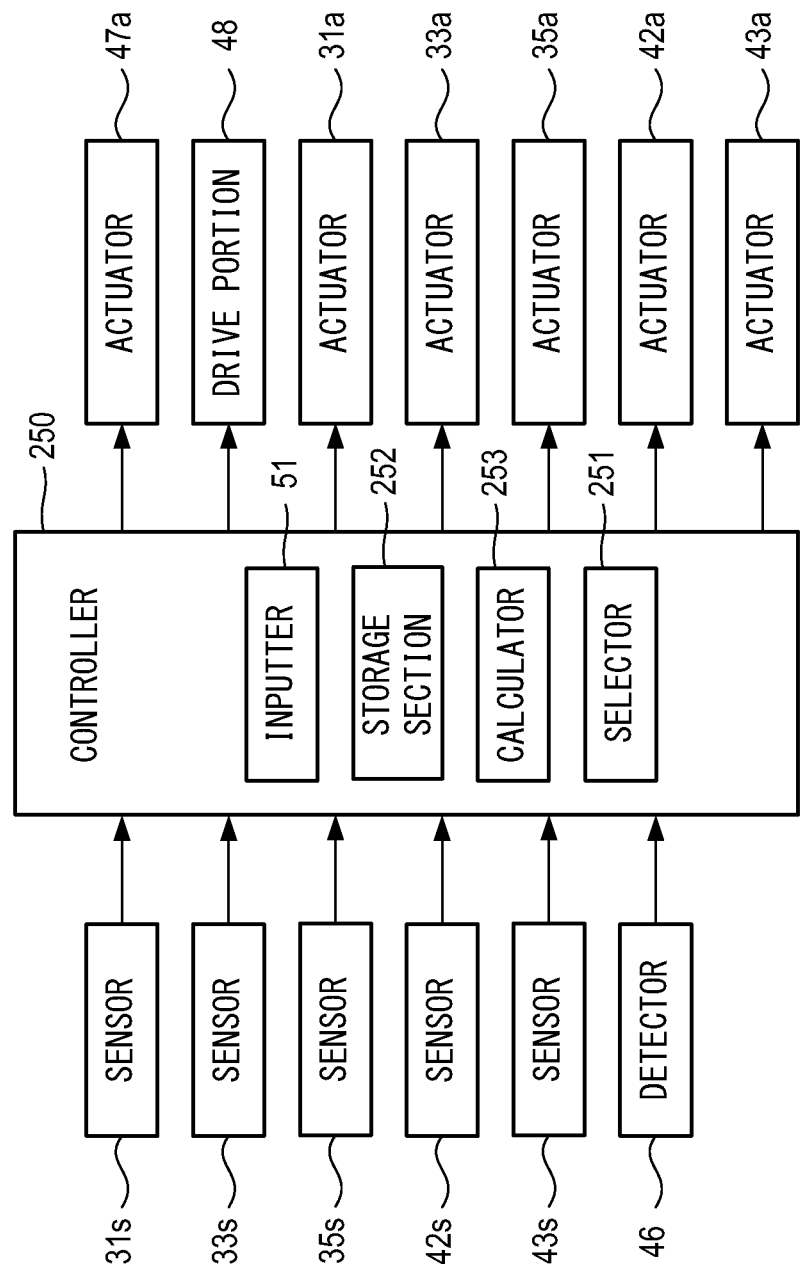
FIG. 7 is a block diagram explaining an example of a configuration of a controller of the surgical robot system in FIG. 4.

FIGS. 6-7 illustrate another example of a configuration of a surgical robot system according to various embodiments. A basic configuration of the surgical robot system of FIGS. 6-7 is similar to that of the embodiment described with reference to FIGS. 1-3 and like reference numbers are used for like elements/components and repeated description thereof is omitted for conciseness. The surgical robot system illustrated in FIGS. 6-7 is adaptable to a different type of trocar. Thus, an explanation will be given of details of the adaptability to a different type of trocar with reference to FIG. 6 and FIG. 7, and explanation of other configuration and so on will be omitted for conciseness.

As shown in FIG. 6, a surgical robot system 201 comprises the surgical instrument 10, the arm device 30, and a controller 250. The controller 250 corresponds to one example of an external force estimation device.

As shown in FIG. 6 and FIG. 7, the controller 250 is an information processor, such as a computer, which comprises a central processing unit (CPU), a ROM, a RAM, an input/output interface, and so on. Program code stored in a storage device, such as the ROM or the RAM, causes the CPU, the ROM, the RAM, and the input/output interface to work cooperatively to function as at least the inputter 51, a selector 251, a storage section 252, and a calculator 253.

The selector 251 is used to identify the trocar 75 to be used in the surgical robot system 1. In some embodiments, multiple types of the trocar 75 may be used in the surgical robot system 1, and information for identifying the trocar 75 of each type is acquired from the storage section 252.

Examples of such a case may include a case where the selector 251 displays on a display of the controller 250 the types of the trocar 75 used in the surgical robot system 1 and stored in the storage section 252 and performs identification by designating a type of the trocar 75 to be used from among the displayed types of the trocar 75, according to an input by a manipulator.

in another example, the trocar 75 to be used may be identified by inputting a model number, a serial number, or the like indicated on the trocar 75 to the selector 251 by a manipulator. A specific method of performing identification is not particularly limited.

The storage section 252 stores in advance information for identifying the trocar 75 to be used in the surgical robot system 1, a value of the resistance force 5Fpx acting between the trocar 75 and the shaft 11 of the surgical instrument 10, and a value of the gravity W acting on the surgical instrument 10. A value of weight may be used as the gravity W. The information for identifying the trocar 75 and the value of the resistance force 5Fpx in the trocar 75 are stored in an associated manner.

The calculator 253 calculates a value of the first external force Fp and a value of the second external force Fr based on the information on the force Fw and the torque Mw inputted to the inputter 51 and based on the value of the resistance force stored in advance in the storage section 252. The calculation in the calculator 253 differs from that in the calculator 53 in that the information for identifying the trocar 75 selected by the selector 251 and the value of the resistance force 5Fpx associated therewith are acquired from the storage section 252 to thereby perform an operation. The calculation other than this point is similar to that of the calculator 53.

The above-described configuration with the storage section 252 and the selector 251 provided thereto makes it possible to calculate the value of the first external force Fp and the value of the second external force Fr using the resistance force 5Fpx corresponding to the trocar 75 to be used, even when the trocar 75 to be used is changed to the trocar 75 different in the resistance force 5Fpx acting between the trocar 75 and the shaft 11. This ability to calculate based on the specific trocar 75 being used results in a reduction of deterioration in accuracy of the value of the first external force Fp and the value of the second external force Fr to be calculated, as compared with a case where the resistance force 5Fpx corresponding to the trocar 75 is not used.

The technical scope of the present disclosure is not limited to the above-described embodiments, and various modifications may be made without departing from the spirit of the present disclosure. For example, the present disclosure may be applied to an embodiment that is an appropriate combination of the above-described embodiments, without being limited to that obtained by applying the present disclosure to the above-described embodiments, and no particular limitation is intended.

For example, in the above-described embodiments, the forceps 12 is provided at the distal end of the shaft 11. However, in other embodiments, other instruments used in endoscope surgery may be provided at the distal end of the shaft 11, etc.

Examples of the endoscopic surgery to which the surgical robot system, the external force estimation device, and the computer readable medium of the present disclosure are applied may include endoscopic surgeries in general in which the surgical instrument 10 is inserted into the body of the patient 70. From among the endoscopic surgeries, gastroenterological surgeries on a large organ, such as a digestive organ, in which an external force is likely to be applied to the surgical instrument 10, thoracic surgeries in which the surgical instrument 10 is inserted in between costal bones, and surgeries for obese patients with a thick abdominal wall are examples of endoscopic surgeries in which the surgical robot system of the present disclosure may be used.

It should be understood that the inventive concept is not limited to the above embodiments, but various other changes and modifications may be made therein without departing from the spirit and scope as set forth in appended claims.

What is claimed is:

1. A surgical robot system comprising:
a surgical instrument including a shaft that is configured to be inserted through a trocar placed in a subject;
an arm device configured to hold the surgical instrument and to move the surgical instrument with respect to the subject;
a detector arranged at the arm device and configured to detect values of forces and torques acting on the surgical instrument; and
a controller configured to calculate a value of a first external force that the surgical instrument receives from the trocar and a value of a second external force that the surgical instrument receives from an object other than the trocar and that is abuttable on the surgical instrument, based on the values of the forces and torques, and based on a value of a resistance force acting between the trocar and the shaft, and configured to control the arm device to move the surgical instrument, based on the value of the first external force and the value of the second external force, wherein the surgical robot system further comprises:
a treatment tool provided at a distal end of the shaft of the surgical instrument:
a drive portion configured to drive the treatment tool of the shaft of the surgical instrument; and
a distal end external force detector configured to detect a value of a distal end external force acting on the treatment tool at the distal end of the surgical instrument,
wherein the arm device comprises a holder configured to hold the surgical instrument,
wherein the detector is arranged between the drive portion and the holder, and
wherein the controller calculates a value of a shaft external force that is an external force in the shaft received from an object other than the treatment tool and the trocar and that is abuttable on the surgical instrument, based on the value of the second external force and the value of the distal end external force, and controls the arm device to move the surgical instrument, based on the value of the first external force, the value of the second external force, and the value of the shaft external force.

2. The surgical robot system according to claim 1, wherein the detector detects the values of:
a length-direction force acting in a length direction of the shaft,
a length-direction torque acting about the length direction,
a first intersecting-direction force acting in a first intersecting direction that intersects with the length direction,
a first intersecting-direction torque acting about the first intersecting direction,
a second intersecting-direction force acting in a second intersecting direction that intersects with the length direction and with the first intersecting direction, and
a second intersecting-direction torque acting about the second intersecting direction; and
the controller is configured to calculate the value of the first external force that the surgical instrument receives from the trocar and the value of the second external force that the surgical instrument receives from the object other than the trocar and that is abuttable on the surgical instrument, based on the values of the length-direction force, the first intersecting-direction force, the second intersecting-direction force, the length-direction torque, the first intersecting-direction torque, and the second intersecting-direction torque, and based on the value of the resistance force acting between the trocar and the shaft.

3. The surgical robot system according to claim 1, wherein the arm device is configured to move the surgical instrument with six degrees of freedom.

4. The surgical robot system according to claim 1, wherein the arm device comprises:
a rotating portion fixed to a base, the rotating portion comprising a first actuator that generates a driving force to rotate the rotating portion about a vertical axis;
a first arm;
a first arm rotating portion arranged between the rotating portion and the first arm and comprising a second actuator that generates a driving force to rotate the first arm rotating portion about a horizontal axis;

a second arm;
a second arm rotating portion arranged between the first arm and the second arm and comprising a third actuator that generates a driving force to rotate the second arm rotating portion about a horizontal axis;
a gimbal portion arranged between the second arm and the holder and comprising a first joint and a second joint having respective rotation axes which intersect and a fourth actuator and a fifth actuator configured to rotate the first joint and the second joint respectively; and
a drive portion configured to drive the surgical instrument, wherein the detector is provided between the holder and the drive portion.

5. The surgical instrument according to claim 4, wherein the controller controls at least one of the first actuator, the second actuator, the third actuator, the fourth actuator or the fifth actuator, to move the surgical instrument, based on the value of the first external force and the value of the second external force.

6. A surgical robot system comprising:
a surgical instrument including a shaft that is configured to be inserted through a trocar placed in a subject:
an arm device configured to hold the surgical instrument and to move the surgical instrument with respect to the subject:
a detector arranged at the arm device and configured to detect values of forces and torques acting on the surgical instrument:
a controller configured to calculate a value of a first external force that the surgical instrument receives from the trocar and a value of a second external force that the surgical instrument receives from an object other than the trocar and that is abuttable on the surgical instrument, based on the values of the forces and torques, and based on a value of a resistance force acting between the trocar and the shaft, and configured to control the arm device to move the surgical instrument, based on the value of the first external force and the value of the second external force;
a storage section that stores, for each of a plurality of types of trocar, a value of a resistance force that acts between the trocar and the shaft in association with the type of the trocar; and
a selector configured to select a type of the trocar from among the plurality of types of trocars,
wherein the controller acquires, from the storage section, the value of the resistance force for the type of the trocar selected by the selector, and calculates the first external force and the second external force based on the value of the resistance force acquired.

7. An external force estimation device comprising at least one central processing unit configured to at least:
receive values of forces and torques detected by a detector provided at an arm device, the arm device being detachably connected to a surgical instrument having a shaft that is inserted through a trocar placed in a subject;
calculate a value of a first external force that the surgical instrument receives from the trocar and a value of a second external force that the surgical instrument receives from an object other than the trocar and that is abuttable on the surgical instrument, based on the values of the forces and torques, and based on a value of a resistance force acting between the trocar and the shaft; and
transmit, to the arm device, control signals to control the arm device to move the surgical instrument, based on the value of the first external force and the value of the second external force,
wherein the at least one central processing unit is configured to:
receive, from a distal end external force detector, a value of a distal end external force acting on a treatment tool at a distal end of the surgical instrument:
calculate a value of a shaft external force that is an external force in the shaft received from an object other than the treatment tool and the trocar and that is abuttable on the surgical instrument, based on the value of the second external force and the value of the distal end external force, and
transmit, to the arm device, the control signals to control the arm device to move the surgical instrument, based on the value of the first external force, the value of the second external force, and the value of the shaft external force.

8. The external force estimation device according to claim 7, wherein the detector detects the values of:
a length-direction force acting in a length direction of the shaft,
a length-direction torque acting about the length direction,
a first intersecting-direction force acting in a first intersecting direction that intersects with the length direction,
a first intersecting-direction torque acting about the first intersecting direction,
a second intersecting-direction force acting in a second intersecting direction that intersects with the length direction and with the first intersecting direction, and
a second intersecting-direction torque acting about the second intersecting direction; and
the at least one central processing unit is configured to calculate the value of the first external force that the surgical instrument receives from the trocar and the value of the second external force that the surgical instrument receives from the object other than the trocar and that is abuttable on the surgical instrument, based on the values of the length-direction force, the first intersecting-direction force, the second intersecting-direction force, the length-direction torque, the first intersecting-direction torque, and the second intersecting-direction torque, and on the value of the resistance force acting between the trocar and the shaft.

9. The external force estimation device according to claim 7, wherein the arm device comprises:
a drive portion configured to drive a treatment tool of the shaft of the surgical instrument,
wherein the arm device comprises a holder configured to hold the surgical instrument, and
wherein the detector is arranged between the drive portion and the holder.

10. The external force estimation device according to claim 7, wherein the arm device comprises:
a rotating portion fixed to a base, the rotating portion comprising a first actuator that generates a driving force to rotate the rotating portion about a vertical axis;
a first arm;
a first arm rotating portion arranged between the rotating portion and the first arm and comprising a second actuator that generates a driving force to rotate the first arm rotating portion about a horizontal axis;

a second arm;

a second arm rotating portion arranged between the first arm and the second arm and comprising a third actuator that generates a driving force to rotate the second arm rotating portion about a horizontal axis;

a holder;

a gimbal portion arranged between the second arm and the holder and comprising a first joint and a second joint having respective rotation axes which intersect and a fourth actuator and a fifth actuator configured to rotate the first joint and the second joint respectively; and a drive portion configured to drive the surgical instrument, wherein the detector is provided between the holder and the drive portion.

11. The external force estimation device according to claim 10, wherein the at least one central processing unit transmits the control signals to control at least one of the first actuator, the second actuator, the third actuator, the fourth actuator or the fifth actuator, to move the surgical instrument, based on the value of the first external force and the value of the second external force.

12. An external force estimation device comprising at least one central processing unit configured to at least:

receive values of forces and torques detected by a detector provided at an arm device, the arm device being detachably connected to a surgical instrument having a shaft that is inserted through a trocar placed in a subject:

calculate a value of a first external force that the surgical instrument receives from the trocar and a value of a second external force that the surgical instrument receives from an object other than the trocar and that is abuttable on the surgical instrument, based on the values of the forces and torques, and based on a value of a resistance force acting between the trocar and the shaft; and transmit, to the arm device, control signals to control the arm device to move the surgical instrument, based on the value of the first external force and the value of the second external force, wherein the external force estimation device further comprises:

a storage section that stores, for each of a plurality of types of trocars, a value of a resistance force that acts between the trocar and the shaft in association with the type of the trocar, wherein the at least one central processing unit is further configured to:

select a type of the trocar from among the plurality of types of trocars, acquire, from the storage section, the value of the resistance force for the type of the trocar that is selected, and calculate the first external force and the second external force based on the value of the resistance force acquired.

13. A non-transitory computer readable storage medium that stores program code which, when executed by one or more processors, causes the one or more processors to at least:

receive values of forces and torques detected by a detector provided at an arm device, the arm device being detachably connected to a surgical instrument having a shaft that is inserted through a trocar placed in a subject;

calculate a value of a first external force that the surgical instrument receives from the trocar and a value of a second external force that the surgical instrument receives from an object other than the trocar and that is abuttable on the surgical instrument, based on the values of the forces and torques, and based on a value of a resistance force acting between the trocar and the shaft;

transmit, to the arm device, control signals to control the arm device to move the surgical instrument, based on the value of the first external force and the value of the second external force;

receive, from a distal end external force detector, a value of a distal end external force acting on a treatment tool at a distal end of the surgical instrument:

calculate a value of a shaft external force that is an external force in the shaft received from an object other than the treatment tool and the trocar and that is abuttable on the surgical instrument, based on the value of the second external force and the value of the distal end external force, and transmit, to the arm device, the control signals to control the arm device to move the surgical instrument, based on the value of the first external force, the value of the second external force, and the value of the shaft external force.

14. The non-transitory computer readable storage medium according to claim 13, wherein the detector detects the values of:

a length-direction force acting in a length direction of the shaft, a length-direction torque acting about the length direction, a first intersecting-direction force acting in a first intersecting direction that intersects with the length direction, a first intersecting-direction torque acting about the first intersecting direction, a second intersecting-direction force acting in a second intersecting direction that intersects with the length direction and with the first intersecting direction, and a second intersecting-direction torque acting about the second intersecting direction; and the program code causes the one or more processors to calculate the value of the first external force that the surgical instrument receives from the trocar and the value of the second external force that the surgical instrument receives from the object other than the trocar and that is abuttable on the surgical instrument, based on the values of the length-direction force, the first intersecting-direction force, the second intersecting-direction force, the length-direction torque, the first intersecting-direction torque, and the second intersecting-direction torque, and on the value of the resistance force acting between the trocar and the shaft.

15. The non-transitory computer readable storage medium according to claim 13, wherein the arm device comprises:

a rotating portion fixed to a base, the rotating portion comprising a first actuator that generates a driving force to rotate the rotating portion about a vertical axis;

a first arm;

a first arm rotating portion arranged between the rotating portion and the first arm and comprising a second actuator that generates a driving force to rotate the first arm rotating portion about a horizontal axis;

a second arm;

a second arm rotating portion arranged between the first arm and the second arm and comprising a third actuator that generates a driving force to rotate the second arm rotating portion about a horizontal axis;

a holder;

a gimbal portion arranged between the second arm and the holder and comprising a first joint and a second joint having respective rotation axes which intersect and a fourth actuator and a fifth actuator configured to rotate the first joint and the second joint respectively; and a drive portion configured to drive the surgical instrument, wherein the detector is provided between the holder and the drive portion, and wherein the program code further causes the one or more processors to transmit the control signals to control at least one of the first actuator, the second actuator, the third actuator, the fourth actuator or the fifth actuator, to move the surgical instrument, based on the value of the first external force and the value of the second external force.

16. A non-transitory computer readable storage medium that stores program code which, when executed by one or more processors, causes the one or more processors to at least:

receive values of forces and torques detected by a detector provided at an arm device, the arm device being detachably connected to a surgical instrument having a shaft that is inserted through a trocar placed in a subject;

select a type of the trocar from among a plurality of types of trocars;

acquire, from a storage section, a value of a resistance force for the type of the trocar selected, the storage section storing, for each of the plurality of types of trocars, the value of the resistance force that acts between the trocar and the shaft in association with the type of the trocar;

calculate a value of a first external force that the surgical instrument receives from the trocar and a value of a second external force that the surgical instrument receives from an object other than the trocar and that is abuttable on the surgical instrument, based on the values of the forces and torques, and based on the value of the resistance force acquired; and transmit, to the arm device, control signals to control the arm device to move the surgical instrument, based on the value of the first external force and the value of the second external force.

* * * * *